US00PP33125P2

(12) United States Plant Patent
Deng

(10) Patent No.: US PP33,125 P2
(45) Date of Patent: Jun. 1, 2021

(54) ***CALADIUM* PLANT NAMED 'PINK PANTHER'**

(50) Latin Name: ***Caladium* x *hortulanum***
Varietal Denomination: Pink Panther

(71) Applicant: Florida Foundation Seed Producers, Inc., Marianna, FL (US)

(72) Inventor: Zhanao Deng, Riverview, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/974,071

(22) Filed: Sep. 21, 2020

(51) Int. Cl.
*A01H 5/02* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/02
See application file for complete search history.

(56) References Cited

U.S. PATENT DOCUMENTS

| | | | |
|---|---|---|---|
| PP8,526 | P | 12/1993 | Wilfret |
| PP13,136 | P2 | 10/2002 | Wilfret |
| PP20,792 | P3 | 2/2010 | Deng et al. |

*Primary Examiner* — Keith O. Robinson
(74) *Attorney, Agent, or Firm* — Katherine Koenig; Koenig IP Works, PLLC

(57) ABSTRACT

A new and distinct cultivar of *Caladium* plant named 'Pink Panther', characterized by its unique combination of leaf characteristics, including wide lance-shaped leaves, upright and sturdy petioles, deep pink main veins and primary veins, light pink blotches, slightly ruffled margins, resistance of sunburns and *Xanthomonas* bacterial leaf blight, high tuber yield potential, and excellent performance in containers and shady or sunny landscapes.

6 Drawing Sheets

Genus and species: *Caladium* x *hortulanum.*
Cultivar denomination: 'Pink Panther'.

BACKGROUND OF THE NEW CULTIVAR

The present invention relates to a new and distinct cultivar of *Caladium*, botanically known as *Caladium* x *hortulanum,* and hereinafter referred to by the name 'Pink Panther'. *Caladium* plants are tuberous-rooted plants and typically have attractive heart-shaped or arrow-shaped leaves on long stalks rising directly from the tubers. Foliage may grow in a variety of colors and variegation patterns, and many species have been developed for aesthetic coloration, good container and landscape growth, drought tolerance, pest resistance, and other desirable characteristics.

Plant Breeder's Rights for this cultivar have not been applied for. The new *Caladium* cultivar 'Pink Panther' has not been made publicly available more than one year prior to the filing of this application.

SUMMARY OF THE INVENTION

The new *Caladium* cultivar 'Pink Panther' has not been observed under all possible environmental conditions. The phenotype of the new cultivar may vary with variations in environment and cultural practices such as temperature, light intensity, fertilization, irrigation, and application of plant growth regulators without any change in genotype.

The objective of the breeding program that produced the present cultivar was to develop cultivars that have novel foliar characteristics, produce multiple brightly colored leaves, have good tuber yield potential, and perform well in containers and the landscape. The present *Caladium* cultivar originated from a cross-pollination made in Balm, Fla., in the summer of 2012 between the *Caladium* x *hortulanum* cultivar 'Carolyn Whorton' (not patented), as the female or seed parent, and the *Caladium* x *hortulanum* proprietary breeding line UF4609 (not patented), as the male or pollen parent. The new *Caladium* cultivar was discovered and selected by the inventor as a single plant within the progeny of the stated cross-pollination in Balm, Fla., in the spring of 2014. Breeding line UF4609 was a progeny of a cross made in 2004 between the *Caladium* x *hortulanum* variety 'Cranberry Star' (U.S. Plant Pat. No. 20,792) and the *Caladium* x *hortulanum* variety 'Florida Sweetheart' (U.S. Plant Pat. No. 8,526; patent expired).

Asexual reproduction of the new cultivar 'Pink Panther' by tuber division has been performed annually since 2014. The unique features of this new *Caladium* cultivar are stable and reproduced true to type in successive generations of asexual reproduction.

The following traits have been repeatedly observed and are determined to be the unique characteristic of 'Pink Panther'. These characteristics in combination distinguish 'Pink Panther' as a new and distinct cultivar of *Caladium:*

1. Wide lance or strap-type leaves that have a large deep pink center, deep pink main and primary veins, and irregular blotches of variable sizes and shapes in light pink to white, and ruffled deep green margins;
2. Upright and sturdy petioles and upright plant growth habit;
3. Full yet compact plant habit suitable for planting in containers;

4. Tolerance to *Xanthomonas* bacterial leaf blight and sunburns; and
5. Suitable for shady or sunny landscape locations.

Plant of the new *Caladium* cultivar 'Pink Panther' differ from plants of the female parent, 'Carolyn Whorton', in the following characteristics:

1. Plants of 'Pink Panther' are more compact, and are much shorter and narrower than plants of 'Carolyn Whorton';
2. Leaves of 'Pink Panther' are of the lance-type with a netted palmate venation and with petioles attached to the base, whereas petioles of 'Carolyn Whorton' are attached at within the leaf blade;
3. Leaves of 'Pink Panther' have a deep pink center and deep pink main and primary veins, whereas leaves of 'Carolyn Whorton' have a lighter pink center;
4. Leaves of 'Pink Panther' are smaller than those of 'Carolyn Whorton'; and
5. Bases of leaves of 'Pink Panther' vary from being sagittate, to cordate, to truncate.

Plants of the new *Caladium* cultivar 'Pink Panther' differ from plants of the male parent, breeding line UF4609, in the following characteristics:

1. Plants of 'Pink Panther' are taller and larger than those of breeding line UF4609;
2. Petioles of 'Pink Panther' are sturdy and upright, whereas petioles of breeding line UF4609 are softer; and
3. Leaves of 'Pink Panther' are longer and wider than those of breeding line UF4609, and have a large deep pink center and deep pink main veins.

Plants of the new *Caladium* cultivar 'Pink Panther' can be compared to 'Florida Red Ruffles' (U.S. Plant Pat. No. 13,136). In side-by-side comparisons conducted in Wimauma, Fla., plants of the new *Caladium* cultivar 'Pink Panther' differed from plants of 'Florida Red Ruffles' in leaf coloration and overall plant appearance, with 'Florida Red Ruffles' having dark red leaves and soft petioles.

Plants of the new *Caladium* cultivar 'Pink Panther' can be compared to 'Florida Sweetheart' (U.S. Plant Pat. No. 8,526). In side-by-side comparisons conducted in Wimauma, Fla., plants of the new *Caladium* cultivar 'Pink Panther' differed from plants of 'Florida Sweetheart' in leaf coloration pattern and growth habit, with plants of 'Florida Sweetheart' having leaves that are bright pink in color without any blotches. 'Florida Sweetheart' also has soft petioles and leaves that cascade from the center to the sides of the plant.

DESCRIPTION OF THE FIGURES

The accompanying photographs (as shown in FIGS. 1-6) illustrate the overall appearance of the new *Caladium* cultivar 'Pink Panther'. These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION OF THE CULTIVAR

Figure 1:
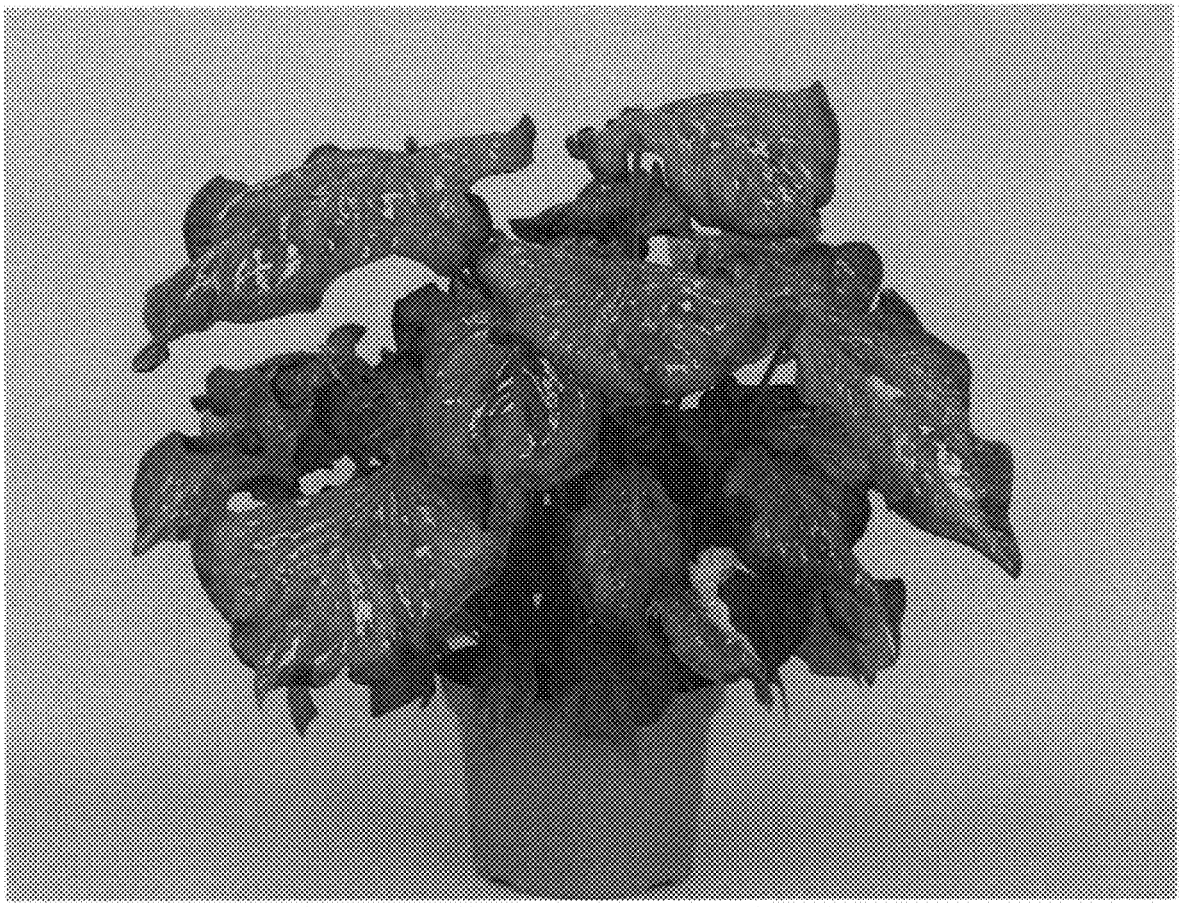
FIG. 1 shows a side perspective view of a typical plant of the new *Caladium* cultivar 'Pink Panther' grown from four No.1-sized (1.5 to 2.5 inches in diameter) intact tubers in a 20.3-cm plastic container in a greenhouse for seven weeks.
Figure 2:
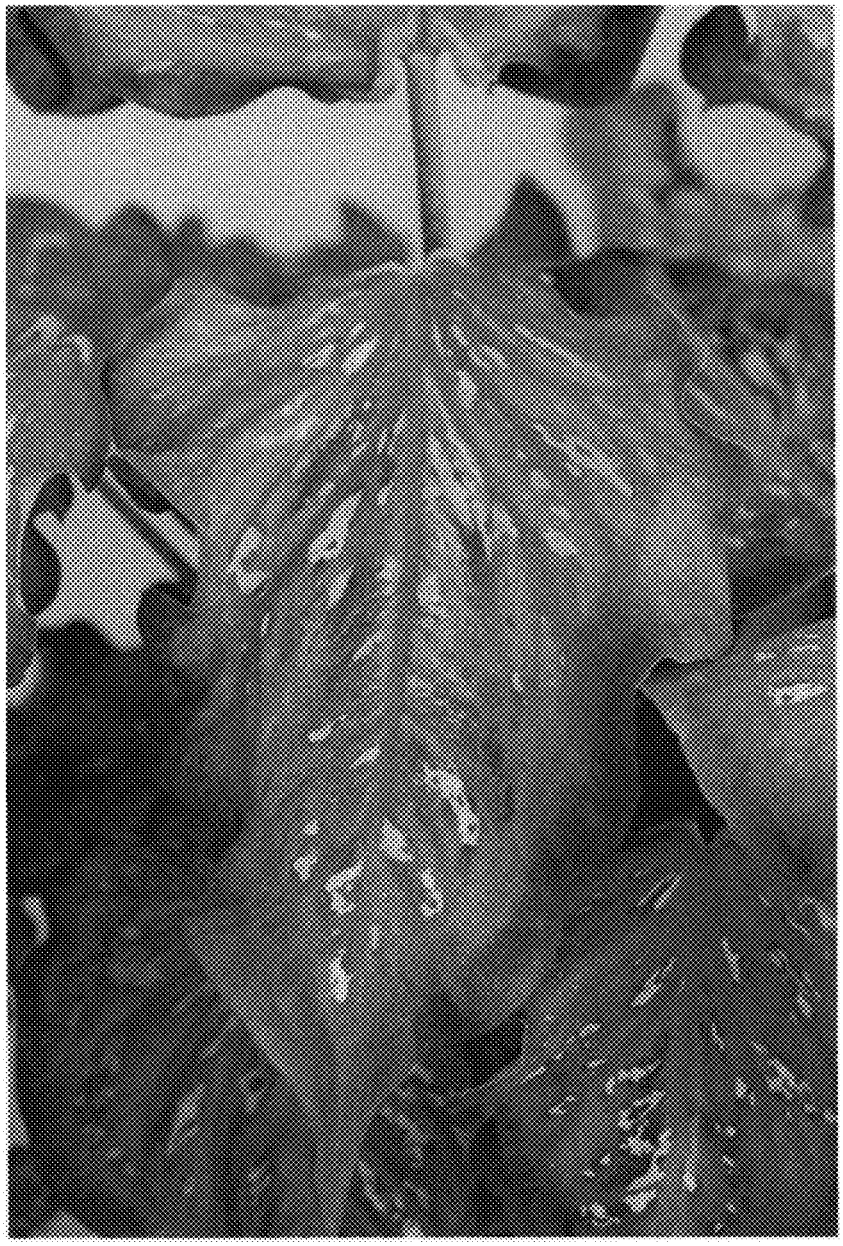
FIG. 2 shows a close-up view of the upper surface of a typical leaf from the new *Caladium* cultivar 'Pink Panther' grown in a greenhouse.

In the following description, color references are made to The Royal Horticultural Society (R.H.S.) Colour Chart, 1986 Edition, except where general terms of ordinary dictionary significance are used.

Description of Growing Conditions

The aforementioned photographs and the following observations and measurements describe plants grown in 20.3-cm containers in Wimauma, Fla., during the summer in a polypropylene-covered greenhouse and plants grown in beds in Wimauma, Fla., during the late summer in an outdoor nursery. All plants were grown under conditions and practices that approximate those generally used in commercial *Caladium* production.

During the production of the plants, day temperatures ranged from about 75° F. to about 93° F., night temperatures ranged from about 66° F. to about 77° F., and light levels were about 30% reduced in the greenhouse or full sun in the outdoor nursery. Plants grown in the greenhouse were about seven weeks from planting tubers when the photographs and the detailed description were taken. Plants grown in the outdoor nursery were about twelve weeks from planting tuber pieces when the photographs and the detailed description were taken.

Botanical Description

Botanical classification:

*Family.*—Araceae.

*Botanical name.*—*Caladium* x *hortulanum.*

*Common name.*—*Caladium* or *Caladium.*

*Cultivar.*—'Pink Panther'.

Parentage:

*Female or seed parent.*—*Caladium* x *hortulanum* cultivar 'Carolyn Whorton' (not patented).

*Male or pollen parent.*—*Caladium* x *hortulanum* breeding line UF4609, which was a progeny of a cross between 'Cranberry Star' (U.S. Plant Pat. No. 20,792) and 'Florida Sweetheart' (U.S. Plant Pat. No. 8,526; patent expired).

Propagation:

*Type.*—By tubers and by tuber divisions.

*Time to initiate roots, summer.*—About seven to ten days at approximately 89.6° F. (approximately 32° C.).

*Time to initiate roots, winter.*—About two to three weeks at approximately 75.2° F. (approximately 24° C.).

Tuber description:

*Number of buds per No. 1-sized (approximately 3.75 cm in diameter) tuber, greenhouse-grown plants.*—About five actively growing buds/shoots.

*Number of buds per No.1-sized (approximately 3.75 cm in diameter) tuber, outdoor nursery-grown plants.*—About four actively growing buds/shoots.

*Height.*—About 2.5 cm.

*Diameter.*—About 3.7 cm.

*Texture.*—Thick, starchy; somewhat brittle.

*Color.*—Epidermis: Between RHS 165A (dark greyed orange) and RHS 165B (medium greyed orange). Interior: Between RHS 5C (yellow) and RHS 6C (yellow).

Root description: Dense, thick, and white (RHS 155D) fleshy roots.

Plant description:

*Type.*—Herbaceous perennial.

*Growth habit.*—Vigorous, upright growth habit with multiple layers of leaves; suitable for 10-cm to 30-cm containers.

*Leaf petioles.*—Arising from tubers, mostly upright, curving outwardly with development.

*Greenhouse-grown plants.*—Plant height, from soil level to top of leaf plane: About 41 cm. Plant height, from soil level to top of inflorescences: About 39 cm. Plant diameter or spread: About 50 cm.

*Outdoor nursery-grown plants.*—Plant height, from soil level to top of leaf plane: About 33 cm. Plant height, from soil level to top of inflorescences: Inflorescences not yet observed. Plant diameter or spread: About 43 cm.

*Cataphylls.*—Observed only on greenhouse-grown plants. Length: About 5 cm. Width: About 0.8 cm. Shape: Linear. Apex: Acute. Base: Sheathing the stem. Color, inner and outer surfaces: RHS 159A (light orange white), speckled with RHS 200C (medium brown) spots.

Foliage description:

*Greenhouse-grown plants.*—Length: About 22 cm. Width (flattened): About 18 cm. Shape: Ovate. Apex: Acuminate to acute. Base: Sagittate to cordate. Margin: Entire; undulate. Texture, upper surface: Smooth, glabrous. Texture, lower surface: Smooth, glabrous; glaucous. Venation pattern: Netted palmate. Color, developing and fully expanded leaves: Upper surface: Center, border, and margins: RHS 137A (medium green) and 137B (medium green); random blotches of RHS 135A or 135B (dark green) and RHS 185C or 185D (medium greyed purple). Basal notch: RHS 185B (dark greyed purple). Venation: Midrib: RHS 185B (dark greyed purple). Primary veins: RHS 185A (dark greyed purple). Lower surface: Center: RHS 138A (medium green) and blotches of RHS 185C or 185D (medium greyed purple). Border and margins: RHS 139B (medium green). Venation, midrib: RHS 161D (light greyed yellow) with streaks of RHS 181C (medium greyed orange). Petiole: Aspect: Mostly erect, curving outwardly with development. Length: About 31 cm. Diameter, distal: About 6 mm. Diameter, proximal: About 12 mm. Strength: Strong, flexible. Color: RHS 29D (medium orange), heavily streaked with RHS 200A or 200B (dark brown). Wing length: About 7 to about 9 cm. Wing diameter: About 7 to about 9 cm. Wing color: RHS 29D (medium orange), lightly streaked with RHS 200D (light brown).

*Outdoor nursery-grown plants.*—Length: About 20 cm. Width (flattened): About 13 cm. Shape: Ovate. Apex: Acuminate to acute. Base: Sagittate to cordate. Margin: Entire; undulate. Texture, upper surface: Smooth, glabrous. Texture, lower surface: Smooth, glabrous; glaucous. Venation pattern: Netted palmate. Color, developing leaves: Upper surface: Center: Variable areas of streaks of RHS 60A (deep red purple) with blotches of RHS 73A (red purple) and RHS 143A (medium green). Border and margins: RHS 143B (light green). Venation, midrib and primary veins: RHS 60A (deep red purple). Lower surface: Center: RHS 60C (deep red purple) or 60D (medium red purple), with blotches of RHS 73B (light red purple) and RHS 143C (light green). Border and margins: RHS 143C (light green). Venation, midrib and primary veins: RHS 146C (medium yellow green). Color, expanded leaves: Upper surface: Center: RHS 60A (deep red purple), with blotches of RHS 74C (red purple) and RHS 147B (dark yellow green). Border and margins: RHS 143A, (medium green), 143B (light green), or 143C (light green) with very thin outer margins of RHS 60A (deep red purple). Venation: RHS 60A (deep red purple). Lower surface: Center: Steaks of RHS 60D (medium red purple), RHS 63D (light red purple), and RHS 147B (dark yellow green) or 147C (medium yellow green). Border and margins: RHS 147B (dark yellow green). Venation: Midrib: RHS 147D (light yellow green), heavily streaked with RHS 60D (medium red purple). Primary veins: RHS 147D (light yellow green). Petiole: Aspect: Mostly erect, curving outwardly with development. Length: About 22 cm. Diameter, distal: About 5 mm. Diameter, proximal: About 9 mm. Strength: Strong, flexible. Color, proximal: RHS 177C (medium greyed orange), heavily streaked with RHS 177A (dark greyed orange). Wing length: About 3 mm. Wing diameter: About 6 mm. Wing color: RHS 29D (medium orange), lightly streaked with RHS 200A (dark brown).

Inflorescence description: Only one inflorescence observed on greenhouse-grown plants.

*Arrangement.*—Upright hooded spathes surrounding a columnar spadix borne on a tall upright scape. Spadix with sessile, simple female and male flowers separated into two zones: female flowers arranged on the lower one-third of the spadix, male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Very few blooms in spring. No data available on longevity.

*Spathe.*—Length: About 16 cm. Width, distal: About 3.5 cm. Width, proximal: About 2.6 cm. Shape: Ovate to somewhat obovate. Apex: Acute to acuminate. Base: Tapering. Margin: Entire; proximal, notched. Texture, upper and lower surfaces: Smooth, glabrous. Color: Front surface: Upper two-thirds: RHS 195D (light greyed green), with streaks of RHS 50A (deep red), RHS 50B (medium red), or RHS 50C (medium red). Lower one-third: RHS 138A or 138B (medium green). Rear surface: Upper two-thirds: RHS 145A (medium yellow green) or RHS 145B (light yellow green), with streaks of RHS 145C (light yellow green) and RHS 50D (light red) near the very top. Lower one third: RHS 144A (medium yellow green), streaked with RHS 144B (light yellow green) and RHS 50B (medium red).

*Spadix.*—Length, entire spadix: About 8 cm. Shape: Spindle-shaped to columnar. Apex: Obtuse. Base: Obtuse. Aspect: Upright. Male flower zone: Length: About 5.8 cm. Diameter: About 8 mm. Color, mature: RHS 158A (light yellow white). Male flowers: Quantity per spadix: About 105. Shape: Obovate. Height: About 4 mm. Diameter: About 2 mm. Anther color: Close to RHS 157D (light green white). Amount of pollen: Little observed. Sterile flower zone: Length: About 1 cm. Diameter: About 5 mm. Color, mature: RHS 158A (light yellow white). Female flower zone: Length: About 0.5 cm. Diameter: About 6 mm. Color: RHS 9C (yellow). Female flowers: Quantity per spadix: About 2. Shape: Obovate. Height: About 4 mm. Diameter: About 3 mm. Stigma color: RHS 9C (yellow). Ovary color: RHS 155D (white).

*Scape.*—Length: About 23 cm. Diameter: About 6 mm at the top and middle, and about 7 mm at the bottom. Strength: Sturdy, flexible. Aspect: Erect. Texture: Smooth, glabrous; glaucous. Color: RHS 199C (dark grey brown) or RHS 199D (medium grey brown), densely streaked with RHS 200B (dark brown) or RHS 200C (medium brown). Just below spathe: RHS 138B (medium green), streaked with RHS 138A (medium green).

*Seeds and fruit.*—Seed and fruit development has not been observed.

Disease Resistance

Plants of the new *Caladium* cultivar 'Pink Panther' have been observed to show resistance to Xanthomonas bacterial leaf blight. In field trials in Florida, the Xanthomonas bacterial leaf blight resistance score of 'Pink Panther' ranged from 3.7 to 4.8 on a scale of 1 to 5, with 1=highly susceptible and 5=strongly resistant.

Sunburn Resistance

Plants of the new *Caladium* cultivar 'Pink Panther' have been observed to show resistance to sunburns. In field trials conducted in Florida, the sunburn resistance score of 'Pink Panther' ranged from 3.0 to 4.7 on a scale of 1 to 5, with 1=highly sensitive and 5=highly resistant to sunburns.

Tuber Yield Potential

'Pink Panther' was evaluated for tuber yield potential in Balm, Fla., in 2018 and 2019. The soil was Eau Gallie fine sand with about 1% organic matter and a pH of between 6.2 and 7.4. *Caladium* plants were grown in the field on white plastic-mulched raised beds. In the 2018 season, ground beds (81 cm in width, 20 cm in height) were fumigated on Feb. 13, 2018, with Pic-Clor 60 (39.0% 1,3-dichloropropene, 59.6% chloropicrin) at 448 $kg \cdot ha^{-1}$ and Prowl® H2O (BASF SE, Germany). *Caladium* seed tubers were treated in hot water (50° C.) for 30 minutes. Seed tuber pieces (approximately 2.5×2.5×2.5 cm) were dusted with a biological fungicide RootShield® Plus WP (BioWorks, Victor, N.Y.) and planted manually on Apr. 27, 2018, with approximately 25.4 cm between-row spacing and approximately 15.2 cm in-row spacing. Fifty pounds of granular nitrogen (50 N) per acre was incorporated into the soil prior to bedding. Two drip tapes were buried under the plastic mulch along the raised beds, which provided the irrigation water and fertilization. Fertigation began on May 29, 2018, injecting a commercial liquid fertilizer (5N-0.87P-6.64K) at the rate of 0.454 kg of nitrogen an acre a day, and stopped on Oct. 31, 2018. New crop tubers were dug and washed on Dec. 17, 2018, and air-dried for approximately 50 days inside a greenhouse. Dried tubers from each experimental field plot were weighed, graded, and counted on Feb. 6, 2019. Tuber grading was by the maximum diameter: Super Mammoth (greater than 11.4 cm), Mammoth (8.9 to 11.4 cm), Jumbo (6.4 to 8.9 cm), No. 1 (3.8 to 6.4 cm), and No. 2 (2.5 to 3.8 cm). Tuber grades and counts were converted into a production index to show the relative economic value of the harvested tubers per field plot: Production index=8 n (Super Mammoth)+6 n (Mammoth)+4 n (Jumbo)+2 n (No.1)+1 n (No.2), where n=number of tubers in the grade. The relative values assigned to the five tuber grades in calculating production index were based on the relative market prices provided by Florida *Caladium* tuber producers.

For the 2019 season, beds were fumigated on Feb. 24, 2019, with Pic-Clor 60 at 448 $kg \cdot ha^{-1}$. *Caladium* seed pieces were planted on Apr. 4, 2019. Fifty pounds of granular nitrogen (50 N) per acre was incorporated into the soil prior to bedding. Fertigation began on Jun. 1, 2019, by injecting a commercial liquid fertilizer (5N-0.87P-6.64K) at 0.454 kg of nitrogen per acre per day. The fertilization rate was increased to 0.908 kg of nitrogen per acre per day on Jul. 24, 2019, and ended on Oct. 31, 2019. Tubers were dug and washed on Dec. 9, 2019, dried in the greenhouse for approximately 45 days, and weighed, graded, and counted on Jan. 21, 2020, using the same protocol that was used in 2018.

In both seasons, field plots were arranged in a randomized complete block design with three replicates. The plot size was 1.2 $m^2$ and was planted with 30 *Caladium* propagules (tuber pieces). In 2018, two cultivars 'UF 4412' (US Plant Pat. No. 25,612; commercially sold under the trade name FAIRYTALE PRINCESS™) and 'UF 4424' (US Plant Pat. No. 25,598; commercially sold under the trade name RED HOT™) were included in the field as checks to assess the tuber yield and plant performance of 'Pink Panther'. In the 2019 season, 'Florida Sweetheart' was included in the trial as a check. Analysis of variance was conducted using the JMP Pro 15.0.0 program, followed by means comparisons using the Tukey-Kramer HSD test (The SAS Institute, Inc., Cary, N.C., 2019).

The number, weight, and production index of marketable tubers (Grade No. 2 to Super Mammoth) produced by 'Pink Panther' in 2018 was 59.0, 1.83 kg, and 87.7, respectively, all significantly higher than those of 'UF 4412' 'UF 4424' (Table 1). The two checks grew very poorly and their tuber weight was only 6% to 9% of the tuber weight of 'Pink Panther'. The reasons for the poor growth and yield of 'UF 4412' and 'UF 4424' remained to be found. It was suspected that these two cultivars might be sensitive to the herbicide Harmony® (FMC Agricultural Caribe Industries, Ltd., Bermuda), which was applied to the bed top and plants in early June 2018 to control weeds in the field. In the 2019 growing season, the number, weight, and production index of marketable tubers for 'Pink Panther' were 46.7, 1.96, and 77.0, respectively. Compared to 'Florida Sweetheart', a high-yielding cultivar, 'Pink Panther' did not show significant differences. As for tuber grade distribution, 'Pink Panther' primarily produced No. 1- or No. 2-sized tubers and a low percentage of Jumbos. This tuber size distribution is typical with lance-leaved cultivars including 'Florida Sweetheart'.

TABLE 1

Tuber weight, marketable number, production index, and grade distribution of 'Pink Panther', 'UF 4412', 'Florida Sweetheart', and/or 'UF 4424' (checks) Caladium plants in experimental field plots in 2018 and 2019. Values presented are means of three plots with 30 propagules planted in a plot of 1.2 $m^2$.

| | Tuber | | | Tuber grade distribution (%) | | |
|---|---|---|---|---|---|---|
| | Weight (kg) | Marketable (no.) | Prediction index | Jumbo | No. 1 | No. 2 |
| Cultivar | | | 2018 | | | |
| 'Pink Panther' | 1.83 a | 59.0 a | 87.7 a | 3.6Ns | 37.2 a | 59.2 b |
| 'UF 4412' | 0.12 b | 8.3 b | 8.3 b | 0 | 0 b | 100.0 a |
| 'UF 4424' | 0.16 b | 6.7 b | 8.0 b | 0 | 21.5 a | 78.5 b |
| P value | 0.0047 | 0.0004 | 0.0010 | 0.1690 | 0.0013 | 0.0017 |
| | | | 2019 | | | |
| 'Pink Panther' | $1.96^{NS}$ | $46.7^{NS}$ | $77.0^{NS}$ | $4.2^{NS}$ | $52.7^{NS}$ | $43.0^{NS}$ |
| 'Florida Sweetheart' | 1.70 | 43.0 | 71.3 | 5.8 | 49.6 | 44.6 |
| P value | 0.6173 | 0.7451 | 0.6937 | 0.6019 | 0.7784 | 0.9995 |

Container Trials

The suitability of 'Pink Panther' for container plant production was evaluated by forcing tubers in 11.4-cm containers (diameter) in spring/summer of 2019. Number 1-sized tubers were planted on May 31, 2019, in the commercial potting mix Pro-Line 4B (Jolly Gardener, Poland Spring, Me.) amended with Osmocote® (Everris International B.V., Netherlands) fertilizer (15N-3.9P-10K, 5-6 months) at 4.3 $kg \cdot m^{-3}$ and Micromax® (Everris International B.V., Netherlands) at 0.48 $kg \cdot m^{-3}$, and plants were grown in a greenhouse with approximately 30% light exclusion. Temperatures in the greenhouse ranged from 25° C. (night) to 33° C. (day). Potted plants were arranged on metal benches, with a pot-to-pot spacing of 0.4 meters, in the greenhouse in a randomized complete block design with seven replicates. Plant height, plant width, number of leaves, and foliar characteristics were recorded on Jul. 23. and Jul. 24, 2019, approximately eight weeks after planting. Quality of the potted *Caladium* plants was rated on a scale of 1 to 5, with 1=very poor, unattractive, totally unacceptable as potted plants with few leaves, and 5=very attractive, full plants with a symmetrical shape, an appropriate height, and many bright, colorful leaves. 'Florida Red Ruffles' and 'Florida Sweetheart' were included as checks in the container trial. ANOVA and mean comparisons were conducted as described above.

Figure 3:
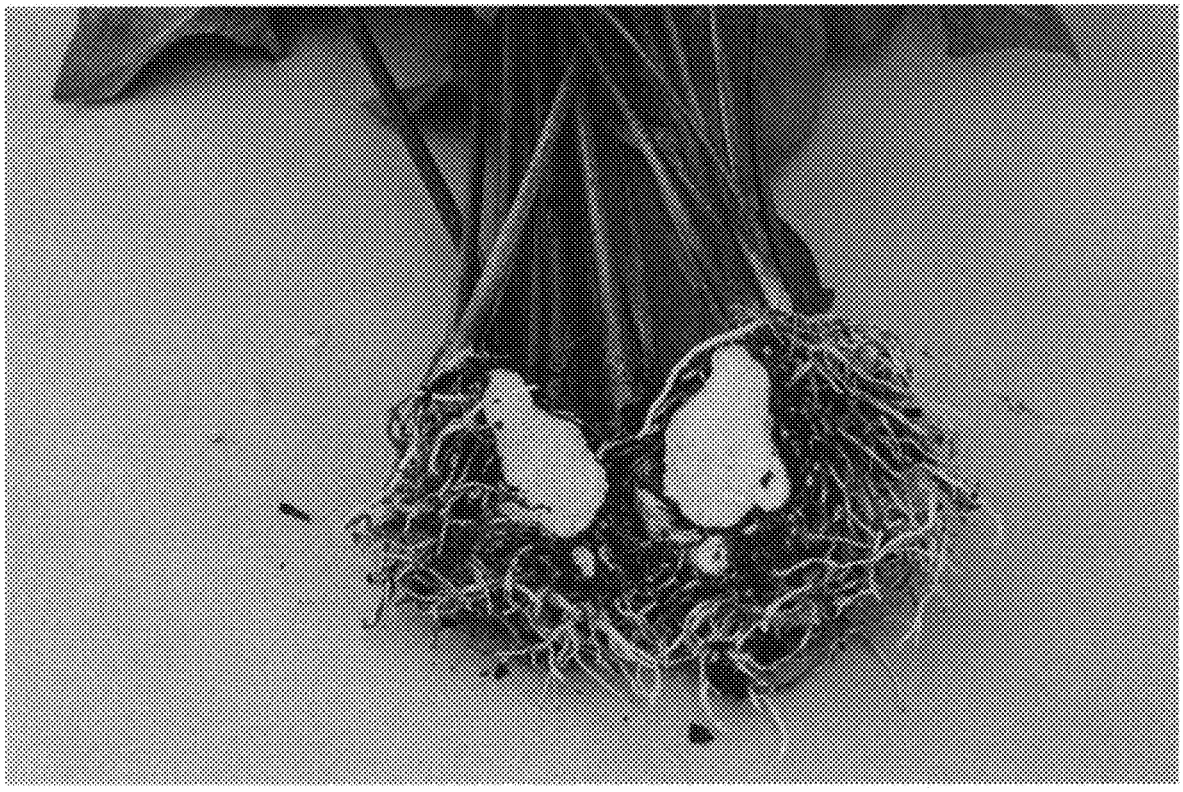
FIG. 3 shows a close-up view of typical leaf petioles, tubers (cutaway view), and roots of the new *Caladium* cultivar 'Pink Panther' grown in a greenhouse.
Figure 4:
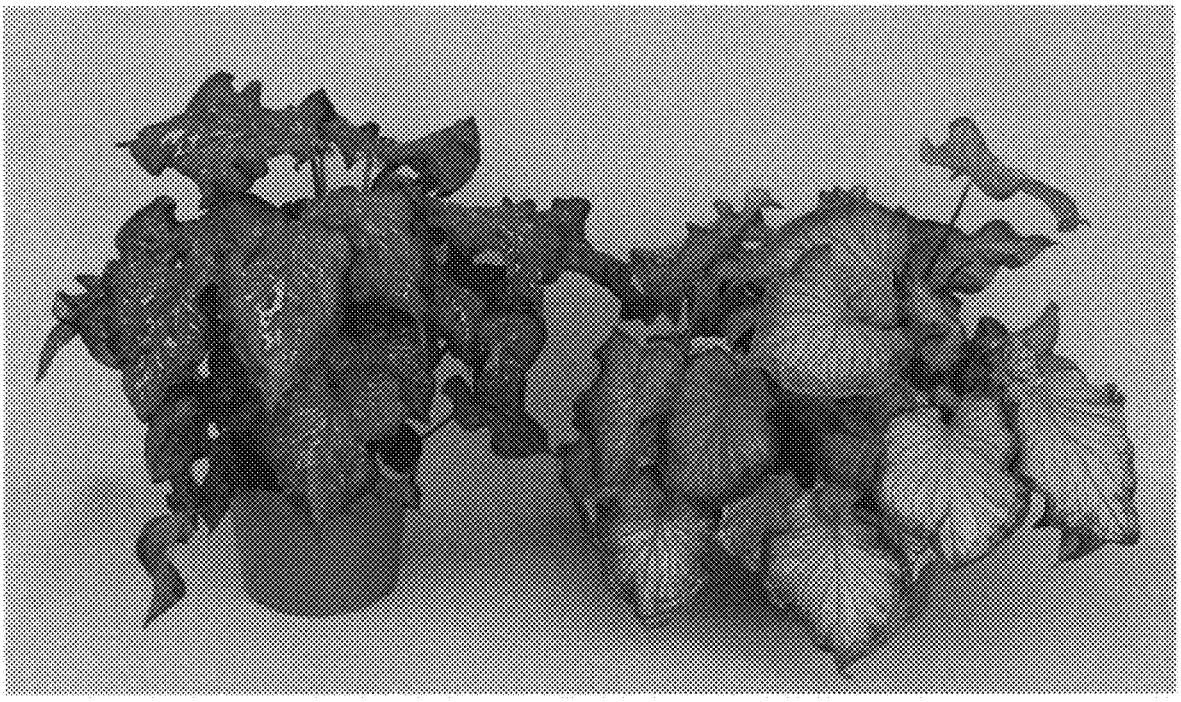
FIG. 4 shows a side perspective view of typical plants of the new *Caladium* cultivar 'Pink Panther' (left) and 'Florida Sweetheart' (right) grown in 20.3-cm plastic containers in a greenhouse for approximately seven weeks.
Figure 5:
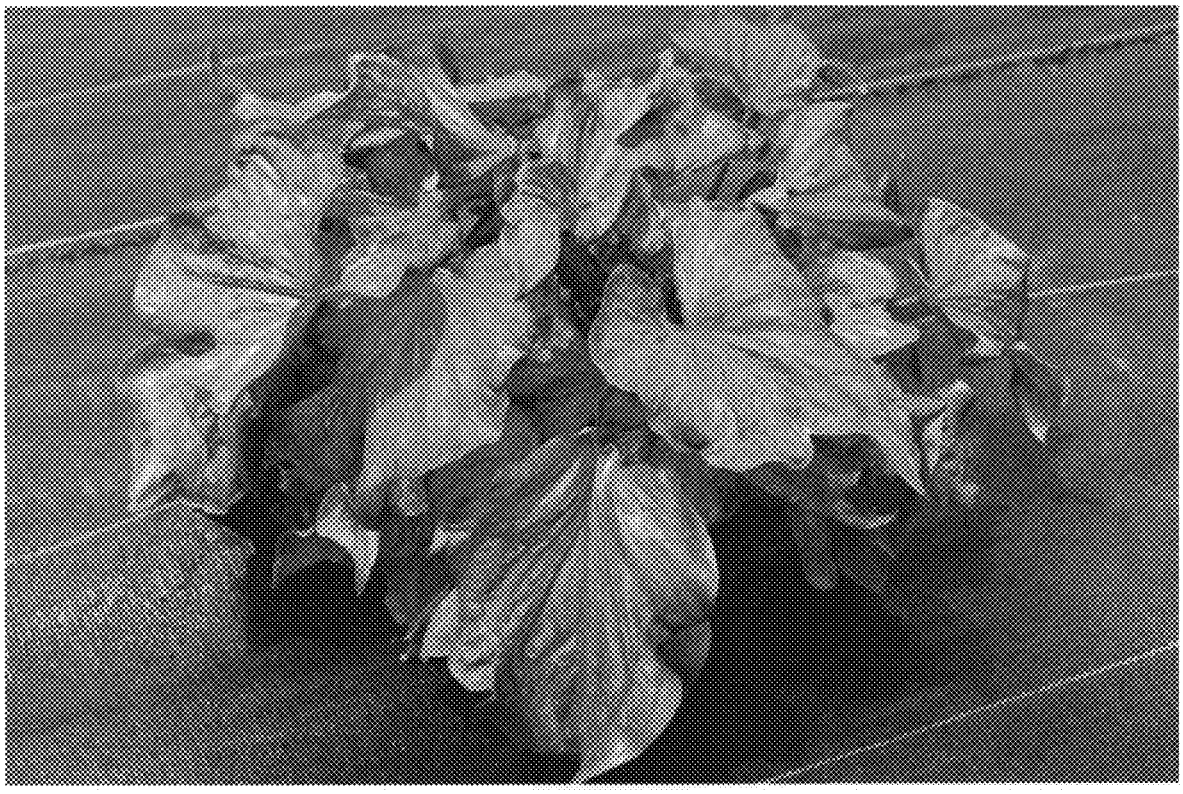
FIG. 5 shows a top view of a typical individual plant of the new *Caladium* cultivar 'Pink Panther' grown from one Jumbo-sized (2.5 to 3.5 inches in diameter) tuber in an outdoor nursery for approximately four months.
Figure 6:
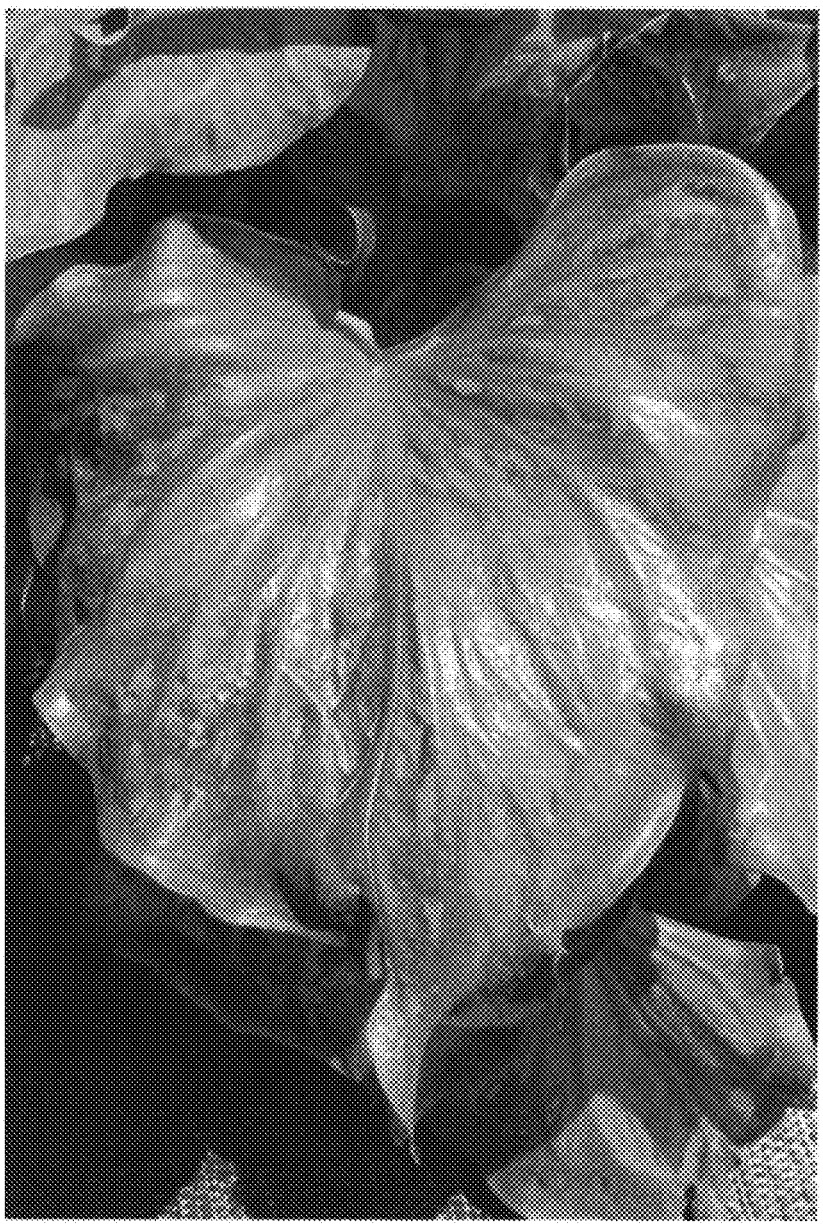
FIG. 6 shows a close-up view of the upper surface of a typical leaf from the new *Caladium* cultivar 'Pink Panther' grown in an outdoor nursery.

Intact and de-eyed 'Pink Panther' tubers sprouted 24 to 27 days after potting up, similar to 'Florida Red Ruffles' (16 to 27 days) but about 7 to 13 days later than 'Florida Sweetheart' (Table 2). 'Pink Panther' plants from intact tubers had an upright growth habit and were 5 to 6 cm taller than 'Florida Red Ruffles' and 'Florida Sweetheart', but did not show significant differences in plant width (34.6 vs. 35.4 or 36.3 cm), leaf number (8.9 vs. 7.4 or 10.7), leaf length (19.1 vs. 18.6 or 19.3 cm) and leaf width (14.0 vs. 4.0 or 14.9 cm), or plant quality rating (2.7 vs. 2.5 or 3.1). Similarly, 'Pink Panther' plants forced from de-eyed tubers did not show significant differences from 'Florida Red Ruffles' and 'Florida Sweetheart' in plant height (19.6 cm) and width (32.2), leaf number (13.9), length (15.1 cm) and width (9.1 cm), and plant quality rating (3.7). Compared to plants from intact tubers, 'Pink Panther' plants forced from de-eyed tubers were approximately 5 cm shorter and narrower (about 2.4 cm) and had five more leaves, and on average leaves were 4 cm shorter and about 5 cm narrower (FIG. 3). Overall, plants from de-eyed tubers had more leaves, more uniformed leaves, and received a higher quality rating (3.7 vs. 2.7). Tuber de-eyeing was beneficial and may be essential for producing high quality pot plants from 'Pink Panther' tubers.

| | Days to sprout | | Plant height (cm) | | Plant width (cm) | |
|---|---|---|---|---|---|---|
| Cultivar | Intact | De-eyed | Intact | De-eyed | Intact | De-eyed |
| 'Pink Panther' | 24.1 a | 26.6 a | 25.4 a | $19.6^{NS}$ | $34.6^{NS}$ | $32.2^{NS}$ |
| 'Red Ruffles' | 26.0 a | 26.9 a | 19.5 b | 20.9 | 35.4 | 33.5 |
| 'Sweetheart' | 10.6 b | 18.7 b | 19.8 b | 17.3 | 36.3 | 35.1 |
| P value | 0.0009 | 0.0473 | 0.0064 | 0.1212 | 0.6423 | 0.5144 |

| | Leaves (no.) | | Leaf length (cm) | | Leaf width (cm) | |
|---|---|---|---|---|---|---|
| Cultivar | Intact | De-eyed | Intact | De-eyed | Intact | De-eyed |
| 'Pink Panther' | $8.9^{NS}$ | 13.9 b | $19.1^{NS}$ | $15.1^{NS}$ | $14.0^{NS}$ | $9.1^{NS}$ |
| 'Red Ruffles' | 7.4 | 17.4 b | 18.6 | 15.8 | 14.0 | 10.3 |
| 'Sweet-heart' | 10.7 | 29.0 a | 19.3 | 13.1 | 14.9 | 8.7 |
| P value | 0.0786 | <0.0016 | 0.8887 | 0.0741 | 0.8075 | 0.4180 |

| | Blooms (no.) | | Quality rating | |
|---|---|---|---|---|
| Cultivar | Intact | De-eyed | Intact | De-eyed |
| 'Pink Panther' | $0.3^{NS}$ | 0 | $2.7^{NS}$ | 3.7 b |
| 'Red Ruffles' | 0 | 0 | 2.5 | 3.7 b |
| 'Sweet-heart' | 0.6 | 0 | 3.1 | 4.4 a |
| P value | 0.0805 | | 0.2050 | <0.0001 |

Tables 2 and 3. Days to sprout (Table 2), plant height (cm) (Table 2), plant width (cm) (Table 2), leaf number (Table 3), leaf length (cm) (Table 3), leaf width (cm) (Table 3), bloom number (Table 3), and plant quality (Table 3) of 'Pink Panther'; 'Florida Red Ruffles', and 'Florida Sweetheart' (checks) *Caladium* plants grown in small containers. No. 1 tubers were planted in 11.4-cm containers (one tuber per container) and grown in a shaded glasshouse in Balm, Fla., in 2019. Values represent the means of seven plants (replicates) produced from intact or de-eyed No. 1 (3.8 to 6.4 cm in diameter) tubers planted individually per container.

We claim:

1. A new and distinct cultivar of *Caladium* plant named 'Pink Panther' as illustrated and described herein.

* * * * *